United States Patent [19]

Timoshenko et al.

[11] 4,164,699

[45] Aug. 14, 1979

[54] THERMOCHEMICAL COMBUSTIBLE GAS DETECTOR

[75] Inventors: Alexandr T. Timoshenko, Makeevka Donetskoi oblasti; Vladimir I. Nazarenko, Donetsk; Felix E. Krigman; Mikhail G. Gusev, both of Makeevka Donetskoi oblasti, all of U.S.S.R.

[73] Assignee: Nauchno-Issledovatelsky Institut Po Bezopasnosti Rabot V Gornoi Promyshlennosti, Makeevka Donetskoi oblasti, U.S.S.R.

[21] Appl. No.: 656,826

[22] Filed: Feb. 9, 1976

[51] Int. Cl.² ............................................. G01N 25/32
[52] U.S. Cl. .................................. 323/75 A; 340/634; 422/96
[58] Field of Search ...................... 23/254 E; 307/310; 323/19, 40, 69, 75 A, 75 E, 75 N; 328/3; 340/237 R, 632–634; 422/96

[56] References Cited

U.S. PATENT DOCUMENTS

| 2,901,740 | 8/1959 | Cutsogeorge | 323/75 N |
| 3,429,178 | 2/1969 | Durbin | 323/75 N |
| 3,678,489 | 7/1972 | Scherban et al. | 340/237 R |
| 4,001,758 | 1/1977 | Esper et al. | 23/254 E |
| 4,002,429 | 1/1977 | Bartovsky | 323/75 N |

*Primary Examiner*—A. D. Pellinen
*Attorney, Agent, or Firm*—Haseltine, Lake & Waters

[57] ABSTRACT

A thermochemical combustible gas detector having a resistor bridge including a thermistor which is sensitive to combustible gases and a thermistor which compensates the effects of unmeasured parameters and components upon the former thermistor. The supply diagonal of the bridge is connected to a power source via a compensating voltage stabilizer having an adjusting link and two amplifier-comparator links one of which is auxiliary. The detector further includes two conventional auxiliary resistors which are interconnected in series and form an additional resistor bridge with the thermistors of the main bridge. The input of the first amplifier-comparator link is connected to the measuring diagonal of the main bridge. The input of the auxiliary amplifier-comparator link is connected either to the measuring diagonal of the additional resistor bridge, or to one of the auxiliary resistors.

3 Claims, 3 Drawing Figures

THERMOCHEMICAL COMBUSTIBLE GAS DETECTOR

The present invention relates to devices for automatic detection of combustible gases and vapors in the atmosphere and, more particularly, to thermochemical combustible gas detectors.

Such devices are extensively used to indicate impermissibly high concentrations of combustible gases and vapors in mining, chemical, petrochemical, gas and other industries.

There is a known thermochemical combustible gas detector comprised of a resistor bridge. Each of the two adjacent arms of this bridge includes a thermistor. One of the latter is sensitive to the presence of combustible gases in the atmosphere, whereas the other is intended to compensate for the effects on said sensitive thermistor of unmeasured parameters and components of the atmosphere (temperature, pressure, speed of motion, the presence of steam and carbon dioxide, etc.). Each of the remaining arms of said bridge includes a conventional resistor. The thermochemical detector under review further includes a semiconductor compensating voltage stabilizer through which the supply diagonal of the bridge is connected to a power source. As is well known, the compensating stabilizer includes an adjusting link and an amplifier-comparator link. The input of the amplifier-comparator link of the stabilizer is connected to the measuring diagonal of the bridge. The thermochemical detector in question still further includes a signal indicator for impermissibly high concentrations of combustible gases in the atmosphere. Arranged at the input of said signal indicator is a threshold circuit (a zero-crossing detector or a comparator) through which the signal indicator is connected to the resistor bridge.

As power is switched on, the voltage in the measuring diagonal of the bridge at once becomes stablized. In the supply diagonal, stabilized voltage appears after the thermistors have been warmed up. The magnitude of this voltage is directly proportional to the voltage of the measuring diagonal because of a certain ratio between the resistances of the thermistors and resistors in the arms of the bridge.

A combustible gas contained in the atmosphere is oxidized on the catalyst of the sensitive thermistor. The result is a rise in the temperature and resistance of said sensitive thermistor and, consequently, a change in the voltage across the supply diagonal of the bridge. As the concentration of the combustible gas increases, this voltage either rises or drops, depending upon the polarity of the voltage being stabilized in the measuring diagonal of the bridge. As the concentration of the combustible gas reaches the maximum this voltage is brought into play and actuates a warning system.

The fact that the supply voltage of the bridge increases with an increase in the combustible gas concentration raises the stability of a detector which operates in an atmosphere where there are possible small concentrations of a combustible gas. This is due to the fact that in the absence of combustible gases, the temperature of the thermistors can be low so that their characteristics are less liable to fluctuations. At the same time, as the concentration of combustible gases reaches a maximum permissible limit, an increase in the voltage makes it possible to raise the temperature of the sensitive thermistor to a value which ensures a required accuracy of determining the concentration of combustible gases.

The fact that the supply voltage of the bridge decreases with an increase in the concentration of combustible gases raises the stability of a detector operating in an atmosphere wherein there may be high concentrations of combustible gases that may even lead to an explosion. This is due to the fact that high concentrations of combustible gases result in intensive heat liberation because of the oxidation of the combustible gas on the sensitive thermistor; a reduced supply voltage of the bridge makes it possible to slow down the rise in the temperature of said thermistor and thus reduce fluctuations of its characteristics. If necessary, in such operating conditions it is possible to ensure a constant temperature of the sensitive thermistor, and even bring down this temperature with an increase in the combustible gas concentration.

The detector under review is disadvantageous in that it is impossible to ensure high operational stability of said detector within a broad range of combustible gas concentrations, because with an increased voltage due to an increase in the concentration of combustible gases, the sensitive thermistor is subjected to the action of high temperatures resulting from high concentrations of combustible gases; in the case of a reduced voltage due to an increase in the concentration of combustible gases, both thermistors are at elevated temperature even in the absence of combustible gases. The latter is due to the fact that, as stated above, a required accuracy of determining the concentration of a combustible gas is attained precisely at elevated temperatures, which necessitates maintaining such temperatures even in the absence of combustible gases in the atmosphere, because the maximum permissible concentrations of combustible gases are, as a rule, quite low.

It is an object of the present invention to provide a thermochemical combustible gas detector having high operational stability within a broad range of combustible gas concentrations.

The foregoing and other objects of the invention are attained by providing a thermochemical combustible gas detector comprising: a resistor bridge one of whose arms includes a thermistor sensitive to combustible gases, whereas the adjacent arm includes another thermistor intended to compensate for the effects upon said sensitive thermistor of other unmeasured parameters and components of the atmosphere, the two remaining arms of the bridge including conventional resistors; a compensating voltage stabilizer through which the supply diagonal of the bridge is connected to a power source, said voltage stabilizer having an adjusting link and an amplifier-comparator link, the input of the amplifier-comparator link of the stabilizer being connected to the measuring diagonal of the resistor bridge; and a signal indicator of impermissible concentrations of combustible gases, wherein the supply diagonal of the resistor bridge includes, in accordance with the invention, two conventional, series-connected, auxiliary resistors whose resistances are greater than those of the thermistors, said auxiliary resistors, as well as the sensitive thermistor and the compensating thermistor, making up an additional resistor bridge, the compensating stabilizer having an auxiliary amplifier-comparator link whose input is connected either to the measuring diagonal of the additional bridge or to one of the auxiliary resistors.

The signal indicator can be connected to the output of the amplifier-comparator link.

The detector of the present invention is advantageous in that it has a high operating stability within a broad range of concentrations of combustible gases and vapors.

Another advantage of the proposed detector consists of the simplicity of its circuitry. dr Other objects and advantages of the present invention will become more apparent from the following detailed description of preferred embodiments when considered with the accompanying drawings, wherein.

Figure 1:
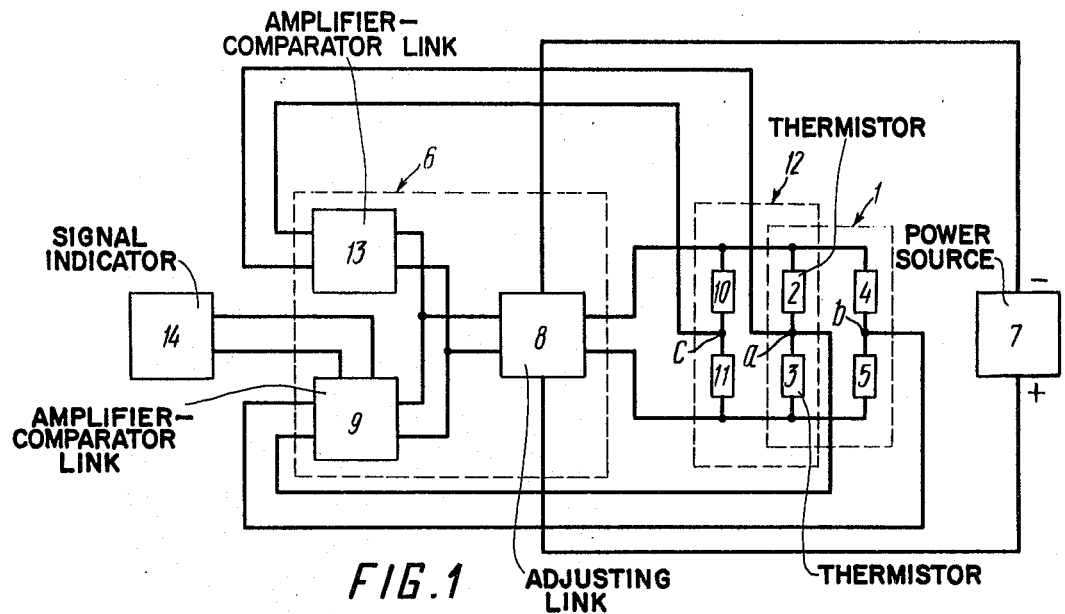
FIG. 1 is a block diagram of a thermochemical combustible gas detector in accordance with the invention.

Referring now to the accompanying drawings, the proposed thermochemical combustible gas detector comprises a resistor bridge 1 (FIG. 1). Two adjacent arms of said resistor bridge 1 include thermistors 2 and 3, respectively. One of the latter, for example, the thermistor 2, is sensitive to the presence of combustible gases in the atmosphere, whereas the other thermistor 3 is intended to compensate for the effects of unmeasured parameters and components of the atmosphere upon the sensitive thermistor 2. The two remaining adjacent arms of said bridge 1 include conventional resistors 4 and 5, respectively.

The sensitive thermistor 2 may be, for example, a coil, preferably of platinum wire which at a certain temperatures acts as a catalyst for combustible gases and vapors. The compensating thermistor 3 is also a platinum wire coil. In order to avoid the catalytic action of the thermistor 3, the latter is coated with a catalytically inert compound. The same effect can be attained by making the thermistor 3 from thick wire in order to reduce its temperature to a point at which platinum is inert, or by using a greater winding pitch in said thermistor 3 than that of the sensitive thermistor 2.

In order to bring down the working temperature of the sensitive thermistor 2 and prolong its service life, thermistor 2 can be coated with a thin film of a catalytically active compound which accounts for a lower oxidation temperature of combustible gases, as compared to platinum. In this case the compensating thermistor 3 needs no coating.

An alternative embodiment of said thermistors is platinum coils arranged either inside or on the surface of cylinders of a porous material, preferably active aluminum oxide. The coils can also be arranged in spherical granules of the same porous material. In order to ensure catalytic activity of the sensitive thermistor, the latter is treated with a catalytic compound.

According to the invention, the supply diagonal of the resistor bridge 1 includes two conventional, series-connected auxiliary resistors 10 and 11. Together with the thermistors 2 and 3, resistors 10 and 11 make up an additional bridge 12. The proposed thermochemical combustible gas detector further includes a semiconductor compensating voltage stabilizer 6 through which the supply diagonal of the resistor bridge 1 is connected to a power source 7. The stabilizer 6 is of the widely known type and normally includes an adjusting link 8 and an amplifier-comparator link 9. The input of the amplifier-comparator link 9 is connected to the measuring diagonal (points "a" and "b") of the bridge 1.

Figure 2:
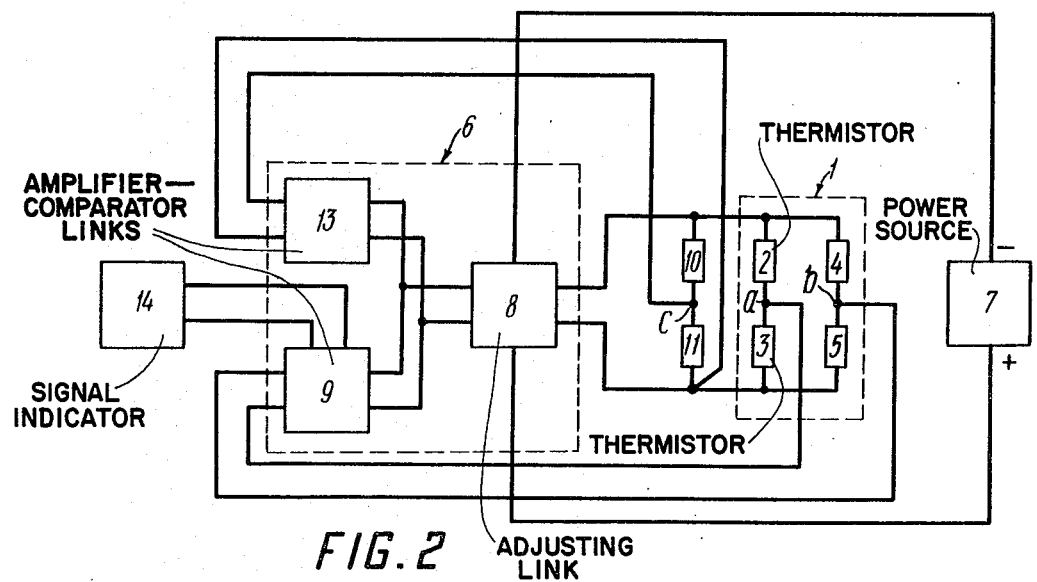
FIG. 2 is a block diagram of another embodiment of the detector in accordance with the invention.

According to the invention, the compensating voltage stabilizer 6 is provided with an auxiliary amplifier-comparator link 13 whose input is connected either to the measuring diagonal (points "a" and "c" of FIG. 1) of the additional bridge 12, or to one of the auxiliary resistors 10 and 11, for example, the resistor 11 (FIG. 2).

The auxiliary resistors 10 and 11 and the auxiliary amplifier-comparator link 13 provide for stable operation of the proposed thermochemical combustible gas detector within a wide range of combustible gas concentrations.

The adjusting link 8 can be built around a common-emitter or a common-collector transistor (the transistor may also be composite). The adjusting link 8 can also be built around transistors of different conductivities.

The function of the amplifier-comparator links 9 and 13 of the compensating voltage stabilizer 6 may be performed by different types of semiconductor d.c. amplifiers having at their inputs either tunnel diodes or reference voltage sources built around, for instance, semiconductor avalanche diodes with resistor voltage dividers.

The thermochemical detector of the present invention further includes a signal indicator 14 of combustible gas concentrations that are in excess of a maximum permissible concentration. According to the invention, in the case when the compensating stabilizer 6 includes the auxiliary amplifier-comparator link 13, the signal indicator 14 can be connected to the output of one of the amplifier-comparator links 9 and 13 of stabilizer 6, for example, to the amplifier-comparator link 9.

This considerably simplifies the signal indicator 14, for in this case the latter can dispense with the threshold circuit.

The function of said signal indicator 14 may be performed by a semiconductor d.c. amplifier at whose output there are a signal lamp and an audio oscillator connected to a loud-speaker. In order to produce an intermittent signal (which is the most effective), the amplifier may be replaced by a multivibrator. The signal indicator can be built into a miner's light whose lamp is used to send an alarm signal in the form of intermittent light. In order to reduce light losses, the power supply of the lamp should be switched with the aid of contacts of an electromagnetic relay whose winding is connected to the output of the multivibrator.

Figure 3:
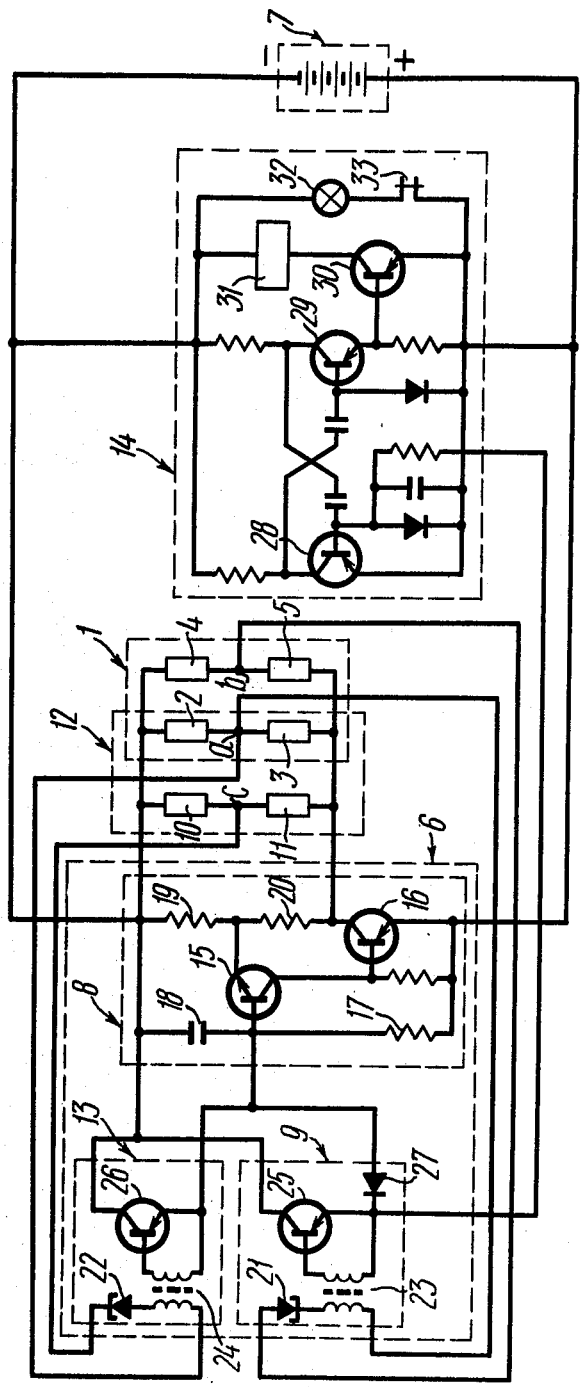
FIG. 3 is a key diagram of said thermochemical combustible gas detector in accordance with the invention.

FIG. 3 is a key diagram of the proposed thermochemical combustible gas detector. In this detector, the adjusting link 8 of the stabilizer 6 is built around two transistors 15 and 16 of different conductivities, transistor 15 being the input transistor, whereas transistor 16 is the output transistor, and an RC circuit composed of a resistor 17 and a capacitor 18. Said RC circuit is connected to the power source 7. In addition, the adjusting link 8 includes a voltage divider built around resistors 19 and 20 and connected to the output of the link 8. The base of transistor 15 is connected to capacitor 18, whereas its emitter is connected to said voltage divider. There is negative feedback between the input and output of the adjusting link 8.

The amplifier-comparator links 9 and 13 are built around tunnel diodes 21 and 22, transformers 23 and 24, and d.c. amplifiers built around transistors 25 and 26, respectively. The tunnel diodes 21 and 22 of said links 9 and 13 are placed in series with the primary windings of the transformers 23 and 24 and make up oscillators; the secondary windings of these transformers are connected to the inputs of the transistors 25 and 26. The inputs of the amplifier-comparator links 9 and 13 are the circuits made up by the tunnel diodes 21 and 22 and the primary windings of the transformers 23 and 24; and outputs of said links 9 and 13 are the emitter-collector circuits of the transistors 25 and 26. Said outputs are connected to the input of the adjusting link 8, in parallel with the capacitor 18. For galvanic isolation of the output circuits of the amplifier-comparator link 9, which are connected to the input of the adjusting link 8 and the input of the signal indicator 14, a diode 27 is included in the output circuit of the link 9, which output circuit is connected to the input of the adjusting link 8.

The signal indicator 14 comprises a multivibrator built around transistors 28, 29 and 30, an electromagnetic relay 31 placed in the collector circuit of the transistor 30, and a signal lamp 32 whose circuit includes contacts 33 of said relay 31.

The proposed detector operates as follows;

As power supply is switched on and in the absence of combustible gases in the atmosphere, voltage is at once stabilized in the measuring diagonal of the bridge 1. This voltage is stabilized as follows; As power supply is turned on, the capacitor 18, arranged at the input of the adjusting link 8 of the stabilizer 6, starts being charged. As a result, voltage goes up across the input and output of the adjusting link 8 and, consequently, in the measuring diagonal of the bridge. The capacitor 18 is charged until voltage in said diagonal reaches a level at which it actuates the oscillator built around the tunnel diode 21 and the primary winding of the transformer 23, which are connected to the input of the amplifier-comparator link 9 connected, in turn, to the measuring diagonal of the bridge 1. As this takes place, the transistor 25 of the amplifier-comparator link 9 is driven into conduction, and its emitter-collector circuit shunts the capacitor 18. The latter is discharged, and voltage in the measuring diagonal of the bridge 1 decreases. The capacitor 18 discharges until voltage in said diagonal is brought down to a level at which the oscillator built around the tunnel diode 21 is no longer in action. After this, the capacitor 18 is charged again, which brings about an increase in the voltage in the measuring diagonal of the bridge 1, etc.

Thus, voltage of a strictly defined magnitude is set in the measuring diagonal of the bridge 1, to which diagonal there is connected the input of the amplifier-comparator link 9. This voltage has a constant component and a variable sawtooth component. Since the levels to which the sawtooth voltage increases or decreases are strictly defined by the oscillator being brought in and out of action, the effective voltage value is only slightly dependent upon the sawtooth voltage frequency. At the same time, said frequency is little dependent upon changes in the parameters of the adjusting link 8, due to the negative feedback between its input and output.

In the supply diagonal of the bridge 1, voltage is stabilized after the sensitive thermistor 2 and the compensating thermistor 3 have been warmed up. As stated above, voltage in the supply diagonal is proportional to that in the measuring diagonal, which proportion is defined by the ratio between the resistances of the thermistors 2 and 3 and those of the conventional resistors 4 and 5 placed in the arms of the bridge 1.

Combustible gas contained in the atmosphere is oxidized on the sensitive thermistor 2, which changes the latter's temperature and resistance and, consequently, changes the voltage in the supply diagonal of the bridge 1. As the concentration of the combustible gas goes up, this voltage may either increase or decrease, depending upon the polarity of the voltage being stabilized in the measuring diagonal of the bridge 1. It should be borne in mind, however, that according to the invention, the thermochemical detector must be adjusted so as to increase voltage in the supply diagonal prior to the appearance of the maximum permissible concentration of combustible gas in the atmosphere. Following the appearance of the maximum permissible concentration of combustible gas in the atmosphere, voltage in the measuring diagonal of the bridge 12 is stabilized, and its polarity must ensure a decrease of voltage in the supply diagonal with increasing concentration of combustible gas.

Under such conditions, when the concentration of combustible gas increases to reach a maximum permissible level, the amplifier-comparator link 9 of the stabilizer 6 is brought into play. The voltage in the measuring diagonal of the bridge 1 is stabilized, and the supply voltage of said bridge 1 increases. Simultaneously, there is an increase in the voltage in the measuring diagonal of the additional bridge 12. Besides, in the course of operation of the amplifier-comparator link 9, negative voltage is applied via the latter's transistor 25 to the base of the transistor 28 of the signal indicator 14, whereby said transistor is saturated and the multivibrator built around the transistors 28, 29 and 30 cannot operate. The relay 31 is not energized, and the signal lamp 32 is continuously lighted, which is proof of the fact that the signal indicator is in good condition.

As the concentration of combustible gas reaches a maximum permissible level, voltage in the measuring diagonal of the bridge 12 is brought to a level at which the auxiliary amplifier-comparator link 13 of the stabilizer 6 is brought into play. As this takes place, voltage in the measuring diagonal of the bridge 12 is stabilized as in the case of the measuring diagonal of the bridge 1; as the concentration of combustible gas continues to increase, the supply voltage of the bridge decreases. This, in turn, reduces the voltage in the measuring diagonal of the bridge 1, whereby the amplifier-comparator link 9 of the stabilizer 6 is brought out of action. The transistor 25 then removes negative voltage from the base of the transistor 28 of the signal indicator 14, and the multivibrator in brought into action. As this takes place, power is periodically supplied to the relay 31 whose contacts make the signal lamp 32 flicker. The latter indicates an impermissibly high concentration of a combustible gas in the atmosphere.

It should be borne in mind that the rate of change in the voltage in the measuring diagonal of the bridge, as compared to the rate of change in the combustible gas concentration, is indicative of the sensitivity of the thermochemical combustible gas detector and depends upon the magnitude of the voltage being stabilized in the measuring diagonal of the bridge. The lesser this voltage, the higher the sensitivity. It is therefore essential that the sensitivity of the detector must ensure maximum possible operational stability of the detector within a broad range of combustible gas concentrations.

Such a stability is ensured if in the absence of combustible gases, the temperature of the sensitive thermistor 2 is kept at a minimum, but is sufficient to detect the presence of combustible gases in the atmosphere. Then, as the combustible gas concentration reaches a maximum permissible level, the temperature of said thermistor 2 is increased to a level at which the concentration of combustible gas can be determined with high accuracy. Finally, with the appearance of explosive concentrations of combustible gas, the temperature of the sensitive thermistor is limited to a level at which no impermissible change in the characteristics of said sensitive thermistor can take place. In cases of high concentrations, it is preferable that the temperature of the sensitive thermistor should be brought down to a lowest permissible level by adjusting the thermochemical detector's circuitry to the maximum sensitivity. It should also be pointed out that reduced temperatures of thermistors account for a prolonged service life therein.

Changes in the parameters and concentrations of unmeasured components of the atmosphere affect the sensitive thermistor 2 and account for additional errors in determining maximum permissible concentrations of combustible gases. Yet these changes equally affect the compensating thermistor 3, whereby said errors are substantially reduced.

As the auxiliary amplifier-comparator link 13 is connected to one of the resistors 10 and 11, for example, to the resistor 11 (FIG. 2), the amplifier-comparator link 9 operates as in the case when there is no combustible gas in the atmosphere, or when the concentration of combustible gas in the atmosphere reaches a maximum permissible level. An increase in the concentration of combustible gas leads to an increase in the voltage in the supply diagonal of the bridge 1 and, consequently, to an increase in the voltage across the resistor 11. As the concentration of the combustible gas reaches a maximum permissible level, the voltage across the resistor 11 reaches a level at which the auxiliary amplifier-comparator link 13 of the stabilizer 13 is brought into action. Voltage across the resistor 11 is stabilized, which equally applies to the voltage in the supply diagonal of the bridge 1; further increase in the concentration of the combustible gas does not change the latter voltage. This makes it possible to limit the temperature increase rate of the thermistors 2 and 3 with impermissibly high concentrations of combustible gases and thus expand the working range of combustible gas concentrations. Since there is no increase in the voltage in the supply diagonal of the bridge 1 with an increase in the combustible gas concentration, an increase in the temperature and resistance of the sensitive thermistor 2 leads to a decrease in the voltage in the measuring diagonal of the bridge 1, whereby the amplifier-comparator link 9 of the stabilizer 6 is disconnected. As a result, a signal is applied to the input of signal indicator 14, and the latter gives an alarm signal.

Thus, the proposed combustible gas detector has a number of important advantages over the known types of detectors. These advantages include high operating stability of the detector within a broad range of combustible gas concentrations, longer service life of the sensitive and compensating thermistors, and a relatively simple circuitry of the detector. All the foregoing factors account for high reliability, simple adjustment and maintenance, and small size and weight of the proposed thermochemical combustible gas detector.

What is claimed is:

1. A thermochemical combustible gas detector comprising:
    a resistor bridge having a first arm including a thermistor sensitive to combustible gases,
    a second arm adjacent to said first arm, said second arm including a thermistor for compensating the effect of unmeasured parameters and components of the atmosphere upon said sensitive resistor,
    a third arm and a fourth arm, each including a conventional resistor;
    an additional resistor bridge having one arm including a conventional auxiliary resistor,
    a second arm including another conventional auxiliary resistor,
    the third and fourth arms of said additional bridge forming said sensitive and compensating thermistors of said first resistor bridge;
    a compensating voltage stabilizer comprising:
    an amplifier-comparator link with input connected to the measuring diagonal of said resistor bridge,
    an auxiliary amplifier-comparator link with input connected to the measuring diagonal of said additional resistor bridge,
    an adjusting link with input connected in parallel to each output of the amplifier-comparator links, an output of said adjusting link being connected to the supply diagonal of both of said bridges;
    a signal indicator of impermissible concentrations of combustible gases in the atmosphere and having an input connected to the output of any of said amplifier-comparator links of said stabilizer;
    a power source connected to said stabilizer and signal indicator.

2. A thermochemical combustible gas detector comprising:
    a resistor bridge having
    a first arm including a thermistor sensitive to combustible gases,
    an adjacent arm including a thermistor for compensating the effects of other unmeasured parameters and components of the atmosphere upon said sensitive thermistor,
    each of two remaining arms of said bridge including a conventional resistor;
    two conventional auxiliary resistors connected in series to the supply diagonal of said resistor bridge;
    a compensating voltage stabilizer comprising:
    an amplifier-comparator link with input connected to the measuring diagonal of said resistor bridge,
    an auxiliary amplifier-comparator link with input connected to any of said auxiliary resistors,
    an adjusting link with input in parallel with the outputs of said amplifier-comparator links, an output of said adjusting link being connected to the supply diagonal of said resistor bridge;
    a signal indicator of impermissible concentrations of combustible gases in the atmosphere and having an input connected to the output of any of said amplifier-comparator links of said stabilizer;
    a power source connected to said stabilizer and said signal indicator.

3. A thermochemical combustible gas detector comprising:
    a power source;
    a resistor bridge having:
    an arm including a thermistor sensitive to combustible gases,
    an adjacent arm including a thermistor for compensating the effects of other unmeasured parameters and components of the atmosphere upon said sensitive thermistor,
    each of two remaining arms of said resistor bridge including a conventional resistor;
    an additional resistor bridge comprising:
    an arm including a conventional auxiliary resistor;

a second arm including another conventional auxiliary resistor, two remaining arms of said additional bridge forming said sensitive and compensating thermistors of said first resistor bridge;

a compensating voltage stabilizer comprising:

an amplifier-comprator link including:

a tunnel diode, a voltage transformer with primary winding in series with said tunnel diode, said tunnel diode and primary winding of the transformer being connected to the measuring diagonal of said first resistor bridge, a transistor with input connected to the secondary winding of said transformer, a diode with cathode connected to the emitter of said transistor and to the latter's output circuit;

an additional amplifier-comparator link including:

a tunnel diode, a voltage transformer with primary winding connected in series with said tunnel diode, said tunnel diode and primary winding of the transformer being connected to the measuring diagonal of said additional resistor bridge, a transistor with input connected to the secondary winding of said transformer, an adjusting link including:

an RC circuit comprising a resistor and a capacitor connected in series and connected to said power source, the capacitor of said RC circuit being connected in parallel via said diode of the first amplifier-comparator link and with the emitter-collector circuit of said transistor of the same link, said capacitor also being directly connected to the emitter-collector circuit of said transistor of the auxiliary amplifier-comparator link, a voltage divider having two resistors connected in series, an output transistor through whose collector circuit said voltage divider and the supply diagonal, which is common for both of said bridges, are connected to said power source, an input transistor with base connected to the capacitor of said RC circuit, the emitter of said transistor being connected to said voltage divider and the collector of said input transistor being connected to the base of said output transistor;

a signal indicator of impermissible concentrations of combustible gases in the atmosphere connected to said power source and comprising:

a transistorized multivibrator with input connected to the emitter of the transistor of said first amplifier-comparator link, an electromagnetic relay connected to the output of said multivibrator, a signal lamp connected to said power source via contacts of said relay.

* * * * *